(12) United States Patent
Nomura (10) Patent No.: US 9,063,064 B2
(45) Date of Patent: Jun. 23, 2015

(54) X-RAY ANALYSIS APPARATUS AND METHOD OF X-RAY ANALYSIS

(71) Applicant: FUJITSU LIMITED, Kawasaki-shi, Kanagawa (JP)

(72) Inventor: Kenji Nomura, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 259 days.

(21) Appl. No.: 13/856,511

(22) Filed: Apr. 4, 2013

(65) Prior Publication Data

US 2013/0336454 A1 Dec. 19, 2013

(30) Foreign Application Priority Data

Jun. 14, 2012 (JP) .................................. 2012-135186

(51) Int. Cl.
*G01N 23/20* (2006.01)
(52) U.S. Cl.
CPC ................................ *G01N 23/20025* (2013.01)
(58) Field of Classification Search
CPC G01N 23/20025; G01N 23/20; G01N 23/207
USPC ............................................. 378/62, 205, 79
See application file for complete search history.

(56) References Cited

U.S. PATENT DOCUMENTS

| | | | | | |
|---|---|---|---|---|---|
| 5,359,640 | A | * | 10/1994 | Fink et al. ........................ | 378/79 |
| 7,016,465 | B2 | * | 3/2006 | Kamegawa ..................... | 378/63 |
| 7,848,489 | B1 | * | 12/2010 | He et al. .......................... | 378/79 |
| 2003/0012334 | A1 | * | 1/2003 | Kurtz et al. ..................... | 378/73 |
| 2005/0084066 | A1 | * | 4/2005 | Kim et al. ....................... | 378/79 |

FOREIGN PATENT DOCUMENTS

| | | |
|---|---|---|
| JP | H5-87748 | 4/1993 |
| JP | H5-188019 | 7/1993 |
| JP | 2005-300305 A1 | 10/2005 |

\* cited by examiner

*Primary Examiner* — Irakli Kiknadze
(74) *Attorney, Agent, or Firm* — Kratz, Quintos & Hanson, LLP (57) ABSTRACT

An X-ray analysis apparatus includes: an X-ray source that emits an X-ray irradiating a specimen; a specimen holding unit that holds the specimen; and an X-ray detecting unit that detects the X-ray diffracted by the specimen; wherein the specimen holding unit includes a second ϕ-axis rotating stage rotating the specimen about a ϕ-axis, a first ϕ-axis rotating stage rotating the entirety of the second ϕ-axis rotating stage about the ϕ-axis, the second ϕ-axis rotating stage being disposed on the first ϕ-axis rotating stage, a ϕ-axis rotating stage that rotates the entirety of the first ϕ-axis rotating stage about a ϕ-axis, an ω-axis rotating stage that rotates the entirety of the χ-axis rotating stage about an ω-axis, and a 2θ-axis rotating stage rotating the X-ray detecting unit about the 2θ-axis, wherein the second ϕ-axis rotating stage unit rotates at a speed higher than that of the first ϕ-axis rotating stage.

20 Claims, 5 Drawing Sheets

X-RAY ANALYSIS APPARATUS AND METHOD OF X-RAY ANALYSIS

CROSS-REFERENCE TO RELATED APPLICATION

This application is based upon and claims the benefit of priority from the prior Japanese Patent Application No. 2012-135186 filed on Jun. 14, 2012, the entire contents of which are incorporated herein by reference.

FIELD

The embodiments discussed herein are related to an X-ray analysis apparatus and a method of X-ray analysis.

BACKGROUND

Figure 1:
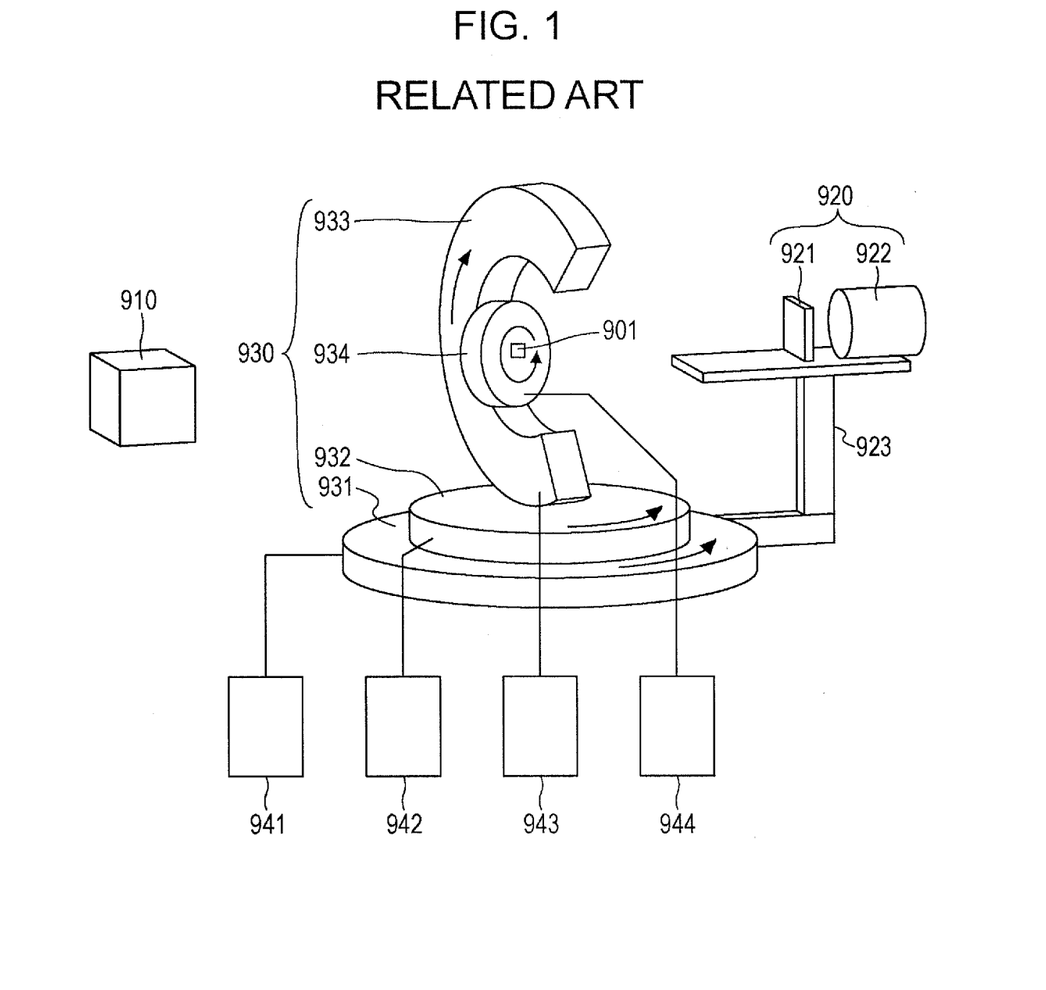
FIG. 1 illustrates the structure of a related-art X-ray analysis apparatus.

In general, when epitaxial films are subjected to, for example, evaluation of distortion, an X-ray diffraction apparatus equipped with four adjustable axes is used as an X-ray analysis apparatus. Specifically, such an X-ray analysis apparatus includes, as illustrated in FIG. 1, an X-ray source 910, a specimen holding unit 930, and an X-ray detecting unit 920. A specimen 901 is held by the specimen holding unit 930, and the X-ray detecting unit 920 detects an X-ray.

The X-ray source 910 emits a so-called homogeneous X-ray. The specimen 901 held by the specimen holding unit 930 is irradiated with the X-ray emitted from the X-ray source 910. The X-ray detecting unit 920 includes a slit 921 and a scintillation detector 922. The X-ray diffracted by the specimen 901 passes through the slit 921 and is detected by the scintillation detector 922. The slit 921 and the scintillation detector 922 are attached to a 2θ arm 923.

The specimen holding unit 930 includes four axis rotating stages, that is, a 2θ-axis rotating stage 931 rotated about a 2θ-axis, an ω-axis rotating stage 932 rotated about an ω-axis, a χ-axis rotating stage 933 rotated about a χ-axis, and a φ-axis rotating stage 934 rotated about a φ-axis. The 2θ-axis rotating stage 931 rotates the 2θ arm 923 about the 2θ-axis. The 2θ-axis rotating stage 931 may be rotated by a 2θ-axis rotation drive unit 941. The ω-axis rotating stage 932 rotates the entire χ-axis rotating stage 933 about the ω-axis. The ω-axis rotating stage 932 may be rotated by a ω-axis rotation drive unit 942. The χ-axis rotating stage 933 rotates the entire φ-axis rotating stage 934 about the χ-axis. The χ-axis rotating stage 933 may be rotated by a χ-axis rotation drive unit 943. The φ-axis rotating stage 934 rotates the specimen 901 about the φ-axis. The φ-axis rotating stage 934 may be rotated by a φ-axis rotation drive unit 944. The 2θ-axis and the ω-axis are coaxial with each other, the φ-axis and the χ-axis are perpendicular to each other, and the χ-axis and the φ-axis are perpendicular to each other.

In general, when the specimen 901 is subjected to, for example, evaluation using such an X-ray analysis apparatus, the four axes, that is, the 2θ-axis, the ω-axis, the χ-axis, and the φ-axis, are adjusted by the 2θ-axis rotating stage 931, the φ-axis rotating stage 932, the χ-axis rotating stage 933, and the φ-axis rotating stage 934. For this purpose, the 2θ-axis rotation drive unit 941, the ω-axis rotation drive unit 942, the χ-axis rotation drive unit 943, and the φ-axis rotation drive unit 944 use pulse motors or the like so as to perform positional control.

In particular, when a film having a good crystallinity and orientation property such as an epitaxial film is formed in the specimen 901, distortion is desirably evaluated with higher resolution. Thus, the following techniques are used: the width of the slit 921 disposed in front of a light incident portion or the scintillation detector 922 is reduced, a double-slit is provided, and a channel cut crystal is used in the light incident portion so as to reduce the divergence angle of the X-ray or reduce the energy width of the X-ray.

In the above-described X-ray analysis apparatus, it takes much time to adjust the four axes, that is, the 2θ-axis, the ω-axis, the χ-axis, and the φ-axis, and accordingly, it takes much time to perform evaluation or the like on the specimen 901. Furthermore, in order to optimize four axial angles for a diffraction peak using an X-ray analysis apparatus such as a high-resolution four-axis X-ray diffraction apparatus, the speed at which an initial value approaches to an optimum value is lower than that of a low-resolution apparatus, and scanning is desirably repeatedly performed for each axis. As a result, measurement takes much time, and accordingly, it is difficult to use a high-resolution four-axis X-ray diffraction apparatus as an inspection apparatus in sites where high-speed inspection is desired such as a manufacturing floor.

Thus, there has been a demand for a high-resolution X-ray analysis apparatus and a high-resolution X-ray analysis method, with which analyses such as evaluation of distortion may be performed in a short time.

An example of related art is Japanese Laid-open Patent Publication No. 2005-300305.

SUMMARY

According to an aspect of the invention, An X-ray analysis apparatus includes: an X-ray source that emits an X-ray, a specimen being irradiated with the X-ray; a specimen holding unit that holds the specimen; and an X-ray detecting unit that detects the X-ray diffracted by the specimen; wherein the specimen holding unit includes a second φ-axis rotating stage that rotates the specimen about a φ-axis using a second φ-axis rotation drive unit, a first φ-axis rotating stage that rotates the entirety of the second φ-axis rotating stage about the φ-axis using a first φ-axis rotation drive unit, the second φ-axis rotating stage being disposed on the first φ-axis rotating stage, a χ-axis rotating stage that rotates the entirety of the first φ-axis rotating stage about a χ-axis, an ω-axis rotating stage that rotates the entirety of the φ-axis rotating stage about an ω-axis, and a 2θ-axis rotating stage that rotates the X-ray detecting unit about the 2θ-axis, wherein the second φ-axis rotation drive unit rotates at a speed higher than that of the first φ-axis rotation drive unit.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Embodiments will be described below. Like elements are denoted by like reference signs and duplicated description thereof is omitted.

First Embodiment

Figure 2:
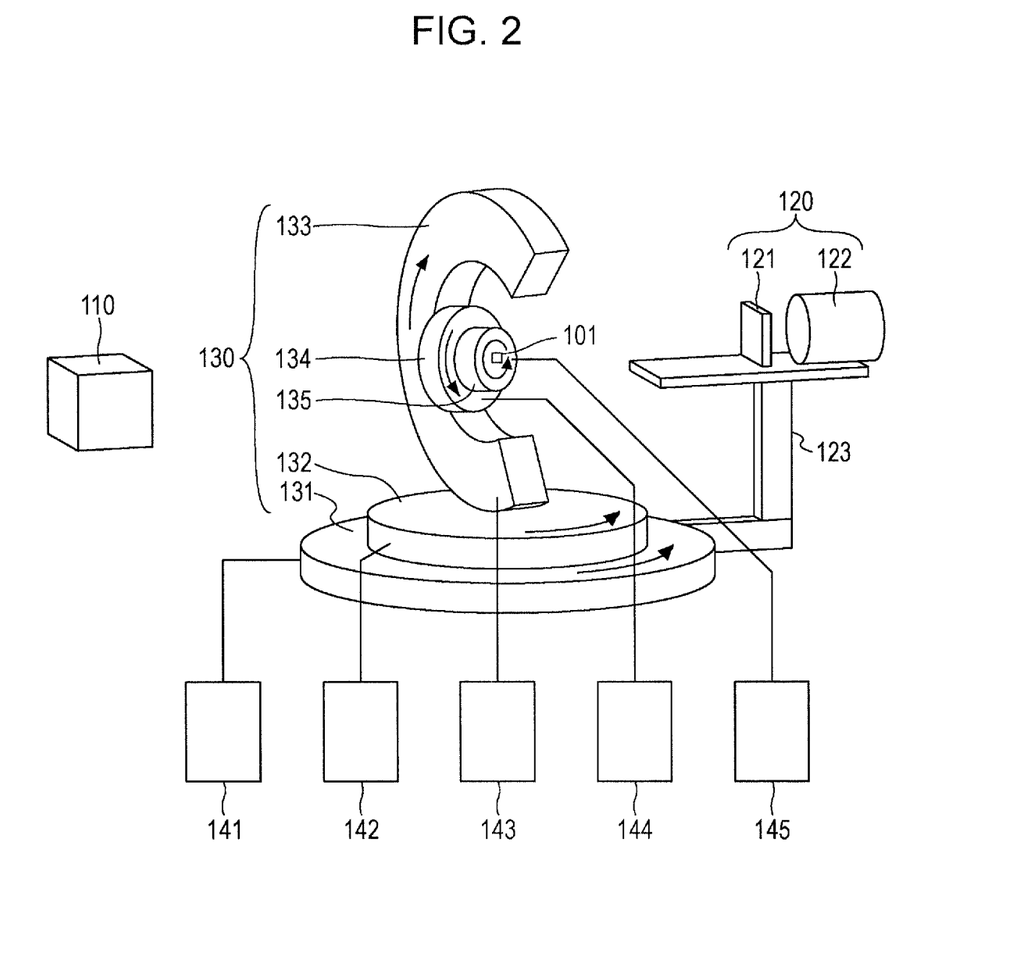
FIG. 2 illustrates the structure of an X-ray analysis apparatus according to a first embodiment.

An X-ray analysis apparatus according to a first embodiment is described. The X-ray analysis apparatus according to the first embodiment includes, as illustrated in FIG. 2, an X-ray source 110, a specimen holding unit 130, and an X-ray detecting unit 120. A specimen 101 is held by the specimen holding unit 130, and the X-ray detecting unit 120 detects an X-ray.

The X-ray source 110 emits a so-called homogeneous X-ray. The specimen 101 held by the specimen holding unit 130 is irradiated with the X-ray emitted from the X-ray source 110. The X-ray detecting unit 120 includes a slit 121 and a scintillation detector, which is an X-ray detector 122. The X-ray diffracted by the specimen 101 passes through the slit 121 and is detected by the X-ray detector 122. The slit 121 and the X-ray detector 122 are mounted on a 2θ arm 123. The X-ray detector 122 may be a device other than the scintillation detector as long as the device may detect an X-ray.

The specimen holding unit 130 includes a 2θ-axis rotating stage 131 rotated about a 2θ-axis, an ω-axis rotating stage 132 rotated about an ω-axis, and a χ-axis rotating stage 133 rotated about a χ-axis. Furthermore, the specimen holding unit 130 includes a first φ-axis rotating stage 134 and a second φ-axis rotating stage 135. The first φ-axis rotating stage 134 and the second φ-axis rotating stage 135 are rotated about a φ-axis. In the X-ray analysis apparatus according to the first embodiment, the second φ-axis rotating stage 135 is disposed on the first φ-axis rotating stage 134, and the specimen 101 is held by the second φ-axis rotating stage 135.

The 2θ-axis rotating stage 131 rotates the 2θ arm 123 about the 2θ-axis. The 2θ-axis rotating stage 131 may be rotated by a 2θ-axis rotation drive unit 141. The ω-axis rotating stage 132 rotates the entire χ-axis rotating stage 133 about the ω-axis. The ω-axis rotating stage 132 may be rotated by an ω-axis rotation drive unit 142. The χ-axis rotating stage 133 rotates the entirety of the first φ-axis rotating stage 134 and the second φ-axis rotating stage 135 about the χ-axis. The χ-axis rotating stage 133 may be rotated by a χ-axis rotation drive unit 143. The first φ-axis rotating stage 134 rotates the entire second φ-axis rotating stage 135 about the φ-axis. The first φ-axis rotating stage 134 may be rotated by a first φ-axis rotation drive unit 144. The second φ-axis rotating stage 135 rotates the specimen 101 about the φ-axis. The second φ-axis rotating stage 135 may be rotated by a second φ-axis rotation drive unit 145. Thus, the specimen 101 may be rotated by the first φ-axis rotating stage 134 about the φ-axis through the second φ-axis rotating stage 135. That is, the specimen 101 may be rotated about the φ-axis by using either of the first φ-axis rotating stage 134 and the second φ-axis rotating stage 135.

In the first embodiment, the 2θ-axis and the ω-axis are coaxial with each other, the ω-axis and the χ-axis are perpendicular to each other, and the χ-axis and the φ-axis are perpendicular to each other. Thus, the φ-axis may be referred to as a first axis, the χ-axis may be referred to as a second axis, and the 2θ-axis and the ω-axis may be referred to as a third axis. In this case, the first axis and the second axis are perpendicular to each other, and the second axis and the third axis are perpendicular to each other. When the axes are referred to as described above, the first φ-axis rotating stage 134 and the second φ-axis rotating stage 135 are rotated about the first axis, and the χ-axis rotating stage 133 is rotated about the second axis. Also, the ω-axis rotating stage 132 is rotated about the third axis, and the 2θ-axis rotating stage 131 rotates the 2θ arm 123 about the third axis.

In the first embodiment, the 2θ-axis rotation drive unit 141, the ω-axis rotation drive unit 142, the χ-axis rotation drive unit 143, and the first φ-axis rotation drive unit 144 use pulse motors or the like so as to perform positional control. The second φ-axis rotation drive unit 145 uses a motor capable of rotating at a speed higher than that of the first φ-axis rotation drive unit 144. The second φ-axis rotation drive unit 145 uses, for example, a motor capable of continuously rotating at high speed.

In general, in an X-ray analysis apparatus, when the specimen 101 is subjected to, for example, evaluation, the four axes, that is, the 2θ-axis, the ω-axis, the χ-axis, and the φ-axis, are adjusted. Here, a case, in which the specimen 101 includes an epitaxial film having been formed, and an asymmetric diffraction peak with the epitaxial film is optimized, is described. Generally in such a case, out of the four axes, that is, the 2θ-axis, the ω-axis, the χ-axis, and the φ-axis, an optimum value with which the intensity is highest is found by repeatedly performing scanning with three axes, that is, the 2θ-axis, the ω-axis, and the φ-axis. The χ-axis is not subjected to the scanning since the optimum value thereof has already been determined in accordance with the diffraction peak. In the first embodiment, optimization of each axis refers to an operation in which an optimum value, at which the intensity is highest, is found for each axis.

In the X-ray analysis apparatus according to the first embodiment, the specimen 101 held by the second φ-axis rotating stage 135 is rotated at high speed by the second φ-axis rotation drive unit 145. In this state, by repeatedly performing scanning with the 2θ-axis and the ω-axis, the optimum values at which the intensity are highest may be found in a short time. That is, a decrease in the number of axes that are repeatedly scanned from three to two allows the optimization with respect to the four axial angles to be performed in a short time, and as a result, the distortion of the specimen 101 may be evaluated in a shorter time. Specifically, an adjustment is performed by rotating the 2θ-axis rotating stage 131 using the 2θ-axis rotation drive unit 141 and rotating the ω-axis rotating stage 132 using the ω-axis rotation drive unit 142 while the specimen 101 is rotated about the φ-axis at high speed. Thus, the distortion of the specimen 101 may be evaluated in a shorter time.

The X-ray analysis apparatus according to the first embodiment is provided with the first ω-axis rotating stage 134 and the first φ-axis rotation drive unit 144, and the second ω-axis rotating stage 135 and the second φ-axis rotation drive unit 145. The reason for this is described as follows. Generally in an X-ray analysis apparatus, the φ-axis is rotated by a pulse motor. When the apparatus features high resolution, operation of the apparatus is slow because a driving angle per pulse is very small. Meanwhile, as described above, when the ω-axis and the χ-axis are scanned while a specimen is rotated in-plane, a step desirably takes one second at the longest. That is, in order to measure the in-plane orientations of the specimen 101 in a uniformed manner, the φ-axis is rotated at a rotational speed of at least one-rotation per second, and ideally at about ten-rotation per second. However, it is difficult to rotate a pulse motor or the like used in a high-resolution apparatus at high speed about the φ-axis.

In order to address this, in the X-ray analysis apparatus according to the first embodiment, the first φ-axis rotating stage 134 and the second φ-axis rotating stage 135 are provided. Such a first φ-axis rotating stage 134 may be rotated by the first φ-axis rotation drive unit 144, which uses a pulse motor or the like capable of performing positional control. Such a second φ-axis rotating stage 135 may be rotated by the second φ-axis rotation drive unit 145 that may rotate at high speed. Thus, in the first embodiment, the distortion of the specimen 101 may be evaluated in a short time. The central position and the rotational axis of the first φ-axis rotating stage 134 desirable match those of the second φ-axis rotating stage 135.

Second Embodiment

Figure 3:
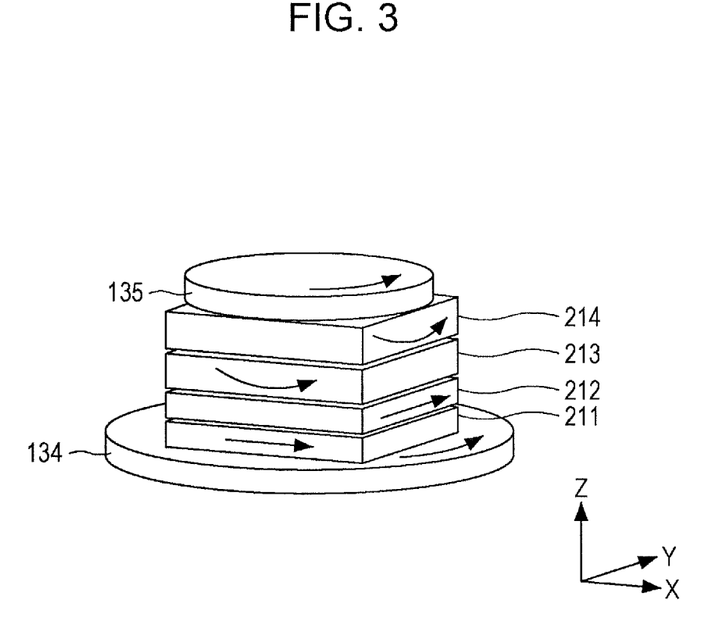
FIG. 3 is an explanatory diagram of an X-ray analysis apparatus according to a second embodiment.

Next, a second embodiment is described. In the second embodiment, the X-ray analysis apparatus according to the first embodiment further features a function of matching the central position and the rotational axis of the first φ-axis rotating stage 134 with those of the second φ-axis rotating stage 135. The X-ray analysis apparatus according to the second embodiment is described with reference to FIG. 3. In the X-ray analysis apparatus according to the second embodiment, an X-axis adjustment stage 211, a Y-axis adjustment stage 212, a swivel Rx-axis adjustment stage 213, and a swivel Ry-axis adjustment stage 214 are provided between the first φ-axis rotating stage 134 and the second y-axis rotating stage 135. The X-axis adjustment stage 211 undergoes a translational movement in an X-axis direction between the first φ-axis rotating stage 134 and the second φ-axis rotating stage 135 so as to perform adjustment. The Y-axis adjustment stage 212 undergoes a translational movement in a Y-axis direction between the first φ-axis rotating stage 134 and the second φ-axis rotating stage 135 so as to perform adjustment. The swivel Rx-axis adjustment stage 213 adjusts inclination in the X-axis direction of the second φ-axis rotating stage 135 relative to the first φ-axis rotating stage 134. The swivel Ry-axis adjustment stage 214 adjusts inclination in the Y-axis direction of the second φ-axis rotating stage 135 relative to the first φ-axis rotating stage 134. As described above, the central position and the rotational axis of the first φ-axis rotating stage 134 may match those of the second φ-axis rotating stage 135 by using the X-axis adjustment stage 211, the Y-axis adjustment stage 212, the swivel Rx-axis adjustment stage 213, and the swivel Ry-axis adjustment stage 214. In the second embodiment, the terms X-axis and Y-axis are used for convenience of description. The X-axis, Y-axis, and the Z-axis are axes perpendicular to one another, and the X-axis and the Y axis correspond to the Z-axis when the φ-axis is assumed to be the Z-axis. The structures and features other than above are similar to those of the first embodiment.

Third Embodiment

X-Ray Analysis Apparatus.

Figure 4:
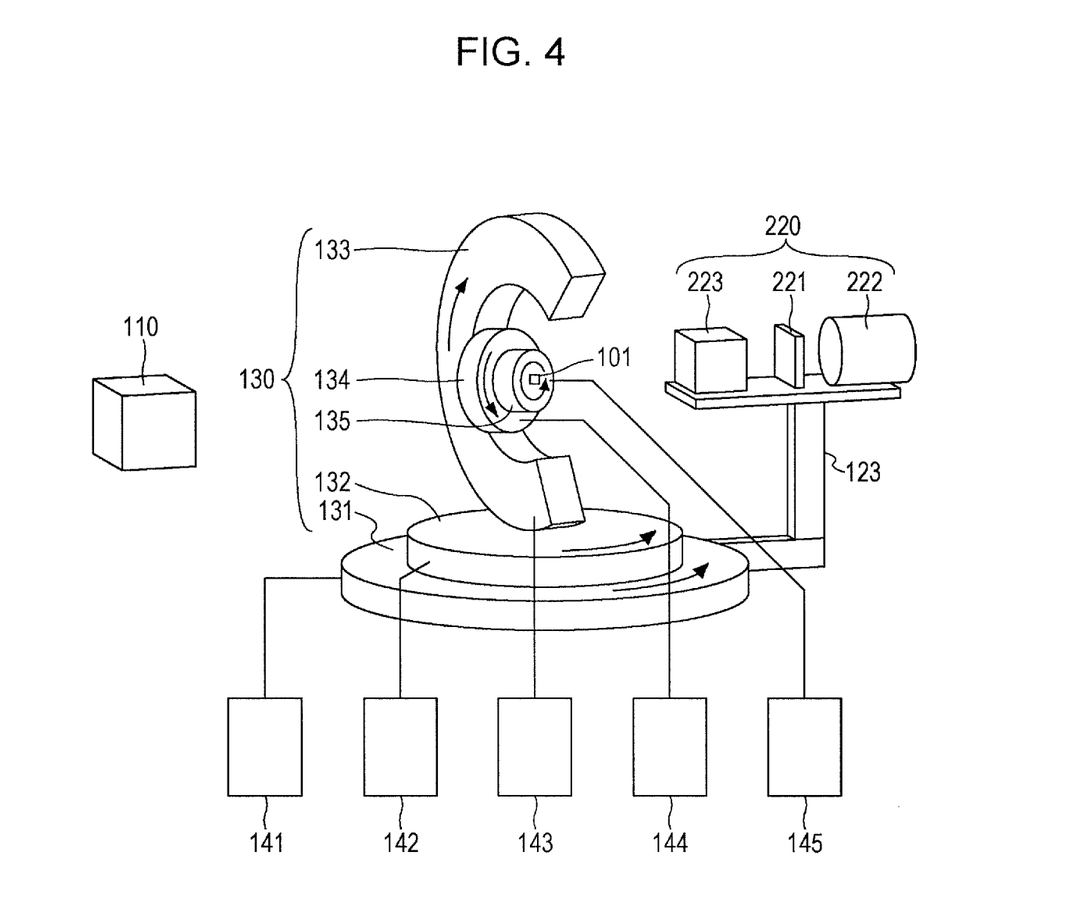
FIG. 4 illustrates the structure of an X-ray analysis apparatus according to a third embodiment.

Next, an X-ray analysis apparatus according to a third embodiment is described. The X-ray analysis apparatus according to the third embodiment includes, as illustrated in FIG. 4, the X-ray source 110, the specimen holding unit 130, and an X-ray detecting unit 220. The specimen 101 is held by the specimen holding unit 130, and the X-ray detecting unit 220 detects an X-ray.

The X-ray source 110 emits a so-called homogeneous X-ray. The specimen 101 held by the specimen holding unit 130 is irradiated with the X-ray emitted from the X-ray source 110. The X-ray detecting unit 220 includes a slit 221, a first X-ray detector 222, and a second X-ray detector 223. The first X-ray detector 222 is similar to the X-ray detector 122 of the first embodiment and uses a scintillation detector or the like.

The second X-ray detector 223 uses a transmissive integrating ionization chamber such as an ionization chamber. The intensity of an X-ray incident on the second X-ray detector 223 may be measured while the X-ray is transmitted through the second X-ray detector 223. In the third embodiment, the second X-ray detector 223, the slit 221, and the first X-ray detector 222 are arranged in this order in a direction in which the X-ray is incident upon the X-ray detecting unit 220 in the X-ray detecting unit 220. Thus, the X-ray incident upon the X-ray detecting unit 220 is detected by the second X-ray detector 223 and, out of the X-ray having been transmitted through the second X-ray detector 223, part of the X-ray having passed through the slit 221 is incident upon the first X-ray detector 222 and detected. In the third embodiment, a slit or the like is not provided in front of the second X-ray detector 223. Thus, with the second X-ray detector 223, an X-ray may be measured at a comparatively large angle. The slit 221, the first X-ray detector 222, and the second X-ray detector 223 are attached to the 2θ arm 123. The first X-ray detector 222 may be a device other than the scintillation detector as long as the device may detect an X-ray.

The specimen holding unit 130 includes the 2θ-axis rotating stage 131 rotated about the 2θ-axis, the ω-axis rotating stage 132 rotated about the ω-axis, and the χ-axis rotating stage 133 rotated about the χ-axis. Furthermore, the specimen holding unit 130 includes the first φ-axis rotating stage 134 and the second φ-axis rotating stage 135. The first φ-axis rotating stage 134 and the second φ-axis rotating stage 135 are rotated about the φ-axis. In the X-ray analysis apparatus according to the third embodiment, the second φ-axis rotating stage 135 is disposed on the first φ-axis rotating stage 134, and the specimen 101 is held by the second φ-axis rotating stage 135.

The 2θ-axis rotating stage 131 rotates the 2θ arm 123 about the 2θ-axis. The 2θ-axis rotating stage 131 may be rotated by the 2θ-axis rotation drive unit 141. The ω-axis rotating stage 132 rotates the entire χ-axis rotating stage 133 about the ω-axis. The ω-axis rotating stage 132 may be rotated by the ω-axis rotation drive unit 142. The χ-axis rotating stage 133 rotates the entirety of the first φ-axis rotating stage 134 and the second φ-axis rotating stage 135 about the χ-axis. The χ-axis rotating stage 133 may be rotated by the χ-axis rotation drive unit 143. The first φ-axis rotating stage 134 rotates the entire second φ-axis rotating stage 135 about the φ-axis. The first φ-axis rotating stage 134 may be rotated by the first φ-axis rotation drive unit 144. The second φ-axis rotating stage 135 rotates the specimen 101 about the φ-axis. The second φ-axis rotating stage 135 may be rotated by the second φ-axis rotation drive unit 145. Thus, the specimen 101 may be rotated by the first φ-axis rotating stage 134 about the φ-axis through the second φ-axis rotating stage 135. That is, the specimen 101 may be rotated about the φ-axis by using either of the first φ-axis rotating stage 134 and the second φ-axis rotating stage 135.

In the third embodiment, the 2θ-axis and the ω-axis are coaxial with each other, the ω-axis and the χ-axis are perpendicular to each other, and the χ-axis and the φ-axis are perpendicular to each other. Thus, the φ-axis may be referred to as the first axis, the χ-axis may be referred to as the second axis, and the 2θ-axis and the ω-axis may be referred to as the third axis. In this case, the first axis and the second axis are perpendicular to each other, and the second axis and the third axis are perpendicular to each other.

In the third embodiment, the 2θ-axis rotation drive unit 141, the ω-axis rotation drive unit 142, the χ-axis rotation drive unit 143, and the first φ-axis rotation drive unit 144 use pulse motors or the like so as to perform positional control.

The second φ-axis rotation drive unit 145 uses a motor that is capable of rotating at a speed higher than that of the first φ-axis rotation drive unit 144. The second φ-axis rotation drive unit 145 uses, for example, a motor that continuously rotates at high speed.

In general, in an X-ray analysis apparatus, when the specimen 101 is subjected to, for example, evaluation, the four axes, that is, the 2θ-axis, the ω-axis, the χ-axis, and the φ-axis, are adjusted. In the X-ray analysis apparatus according to the third embodiment, the second φ-axis rotating stage 135 is rotated at high speed by the second φ-axis rotation drive unit 145 and the second X-ray detector 223 is used. This permits optimization of the ω-axis and the χ-axis to be performed in a short time. In many cases, a right value with respect to the χ-axis may be obtained after scanning has been performed once because the resolution of the χ-axis is generally low.

Method of X-Ray Analysis

Next, a method of X-ray analysis using the X-ray analysis apparatus according to the third embodiment is described. The method of X-ray analysis according to the third embodiment is a method of evaluating the distortion of the specimen 101. In the method, a symmetric diffraction peak is initially optimized, and after that, an asymmetric diffraction peak is optimized. The method of X-ray analysis according to the third embodiment is described with reference to FIG. 5.

Figure 5:
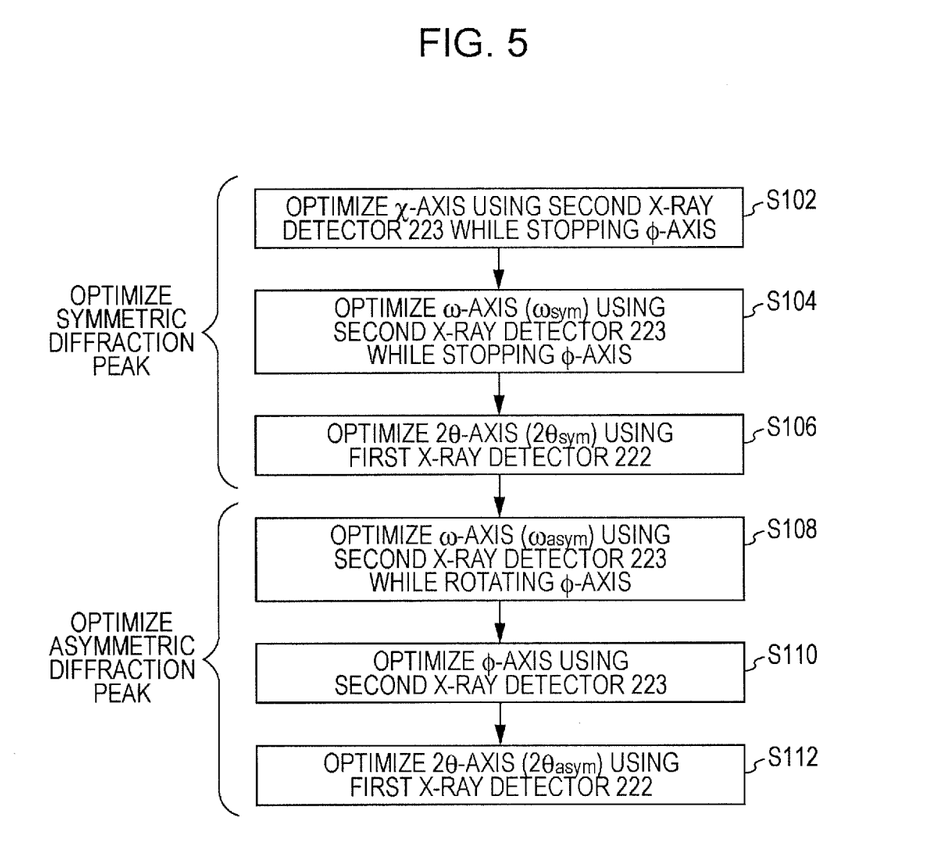
FIG. 5 is an explanatory diagram of a method of X-ray analysis according to the third embodiment.

As described in steps 102 to 106, the symmetric diffraction peak is initially optimized.

First, the χ-axis is optimized in step 102 (S102). Specifically, the χ-axis rotating stage 133 is rotated while the 2θ-axis rotating stage 131, the first φ-axis rotating stage 134, and the second φ-axis rotating stage 135 are stopped so as to optimize the χ-axis in accordance with a value detected by the second X-ray detector 223. In so doing, the ω-axis rotating stage 132 is stopped. As described above, a right value with respect to the χ-axis may be obtained after scanning has been performed once in many cases because the resolution of the χ-axis is generally low.

Next, the ω-axis is optimized in step 104 (S104). Specifically, the ω-axis rotating stage 132 is rotated while the 2θ-axis rotating stage 131, the first φ-axis rotating stage 134, and the second φ-axis rotating stage 135 are stopped so as to optimize the ω-axis ($\omega_{sym}$) in accordance with a value detected by the second X-ray detector 223. In so doing, the χ-axis rotating stage 133 is fixed. After that, an optimum value of the χ-axis may be checked when checking of the optimum value of the χ-axis is desirable.

Next, the 2θ-axis is optimized in step 106 (S106). Specifically, the 2θ-axis rotating stage 131 is rotated while the ω-axis rotating stage 132, the χ-axis rotating stage 133, the first φ-axis rotating stage 134, and the second φ-axis rotating stage 135 are fixed so as to optimize the 2θ-axis ($2\theta_{sym}$). In this 2θ-axis optimization, the 2θ-axis is optimized ($2\theta_{sym}$) in accordance with a value detected by the first X-ray detector 222. Thus, a peak position of a symmetric diffraction peak may be optimized in a short time.

Next, as described in steps 108 to 112, a peak position of an asymmetric diffraction peak is optimized. In order to optimize the peak position of the asymmetric diffraction peak, the value with respect to the χ-axis obtained through optimization of the symmetric diffraction peak may be used for the χ-axis. Thus, actually, it is sufficient that the 2θ-axis, the ω-axis, and the φ-axis be optimized.

The ω-axis is optimized in step 108 (S108). Specifically, the ω-axis is optimized while the second φ-axis rotating stage 135 is rotated at high speed by the second φ-axis rotation drive unit 145. In so doing, the ω-axis rotating stage 132 is rotated while the χ-axis rotating stage 133 is fixed and the 2θ-axis rotating stage 131 and the first φ-axis rotating stage 134 are stopped so as to optimize the ω-axis ($\omega_{asym}$) in accordance with a value detected by the second X-ray detector 223.

Next, the φ-axis is optimized in step 110 (S110). Specifically, the first φ-axis rotating stage 134 is rotated while the ω-axis rotating stage 132 and the χ-axis rotating stage 133 are fixed and the 2θ-axis rotating stage 131 and the second φ-axis rotating stage 135 are stopped so as to optimize the φ-axis in accordance with a value detected by the second X-ray detector 223.

Next, the 2θ-axis is optimized in step 112 (S112). Specifically, the 2θ-axis rotating stage 131 is rotated while the ω-axis rotating stage 132, the χ-axis rotating stage 133, the first φ-axis rotating stage 134, and the second φ-axis rotating stage 135 are fixed so as to optimize the 2θ-axis ($2\theta_{asym}$). In this 2θ-axis optimization, the 2θ-axis is optimized ($2\theta_{asym}$) in accordance with a value detected by the first X-ray detector 222. Thus, the peak position of an asymmetric diffraction peak may be optimized in a short time.

With the method of X-ray analysis according to the third embodiment, the peak position of the symmetric diffraction peak and the peak position of the asymmetric diffraction peak may be optimized in a short time.

The distortion of the specimen 101 may be calculated by using thus obtained 2θ and ω corresponding to the symmetric diffraction peak and the asymmetric diffraction peak. Specifically, when the optimum 2θ corresponding to the symmetric diffraction peak is given by $2\theta_{sym}$, and the optimum 2θ corresponding to the asymmetric diffraction peak is given by $2\theta_{asym}$, the distance $d_{sym}$ between planes in accordance with the symmetric diffraction peak and the distance $d_{asym}$ between planes in accordance with the asymmetric diffraction peak may be calculated from the following expressions (1) and (2) in accordance with Bragg's law. Here, λ indicates the wavelength of the X-ray.

$$d_{sym} = \lambda / (2 \sin(2\theta_{sym}/2)) \quad (1)$$

$$d_{asym} = \lambda / (2 \sin(2\theta_{asym}/2)) \quad (2)$$

Here, distortion $\epsilon_z$ in a direction perpendicular to the substrate surface may be calculated by assigning $d_{sym}$ in the following expression (3). $d_{0sym}$ is the distance between planes in accordance with the symmetric diffraction peak in a completely relaxed state. Thus, it is sufficient that the value be obtained by measuring in advance a specimen that is not distorted.

$$\epsilon_z = (d_{sym} - d_{0sym}) / d_{0sym} \quad (3)$$

Likewise, distortion $\epsilon_z$ in a direction perpendicular to the substrate surface may be calculated by using the asymmetric diffraction peak. In this case, the distance $d_{asym}$ between planes in accordance with the asymmetric diffraction peak is desirably divided into two components, that is, $d_{\perp asym}$, which is the distance between planes in the direction perpendicular to the substrate surface, and $d_{//asym}$, which is the distance between planes in the in-plane direction of the substrate. Here, when the optimum ω corresponding to the symmetric diffraction peak and the optimum optimum ω corresponding to the asymmetric diffraction peak are respectively $\omega_{sym}$ and $\omega_{asym}$, $d_{\perp asym}$ and $d_{//asym}$ are respectively given by the following expressions (4) and (5).

$$d_{\perp asym} = \lambda / [2 \sin(2\theta_{asym}/2) \cos(\omega_{asym} - \omega_{sym} + (2\theta_{sym} - 2\theta_{asym})/2)] \quad (4)$$

$$d_{//asym} = \lambda / [2 \sin(2\theta_{asym}/2) \sin(\omega_{asym} - \omega_{sym} + (2\theta_{sym} - 2\theta_{asym})/2)] \quad (5)$$

Thus, when the asymmetric diffraction peak is used, distortion $\epsilon_z$ in a direction perpendicular to the substrate surface may be calculated also by using the following expression (6).

$$\epsilon_z = (d_{\perp asym} - d_{0\perp asym})/(d_{0\perp asym}) \quad (6)$$

Furthermore, when the asymmetric diffraction peak is used, distortion $\epsilon_x$ in the in-plane direction of the substrate may be calculated by using the following expression (7).

$$\epsilon_x = (d_{//asym} - d_{0//asym})/d_{0//asym} \quad (7)$$

$d_{0\perp asym}$ and $d_{0//asym}$ respectively indicate the distance between planes in the direction perpendicular to the substrate surface and the distance between planes in the in-plane direction of the substrate in accordance with the asymmetric diffraction peak in a completely relaxed state, and may be obtained by measuring in advance a specimen that is not distorted.

With the X-ray analysis apparatus according to the third embodiment, distortion may be calculated by following a determined procedure without repeating scanning. Thus, the X-ray analysis apparatus according to the third embodiment is suitable for automatic measurement. Accordingly, by studying in advance the relationships between the electrical characteristics and the distortion of the formed crystal layer and adding a database, in which these relationships are saved, to the X-ray analysis apparatus of the third embodiment, the distortion of the specimen including a layer having been formed may be automatically inspected and the quality of the specimen may be determined. Furthermore, when a semiconductor production apparatus is equipped with the X-ray analysis apparatus according to the third embodiment, the distortion of the semiconductor layer may be automatically inspected after the semiconductor layer has been formed, and whether or not a desirable semiconductor layer has been formed may be determined in a short time. The structures and features other than above are similar to those of the first embodiment. The structure and features described in the second embodiment may be applied to the present embodiment.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An X-ray analysis apparatus comprising:
   an X-ray source that emits an X-ray, a specimen being irradiated with the X-ray;
   a specimen holding unit that holds the specimen; and
   an X-ray detecting unit that detects the X-ray diffracted by the specimen;
   wherein the specimen holding unit includes
      a second φ-axis rotating stage that rotates the specimen about a φ-axis using a second φ-axis rotation drive unit,
      a first φ-axis rotating stage that rotates the entirety of the second φ-axis rotating stage about the φ-axis using a first φ-axis rotation drive unit, the second φ-axis rotating stage being disposed on the first φ-axis rotating stage,
      a χ-axis rotating stage that rotates the entirety of the first φ-axis rotating stage about a χ-axis,
      an ω-axis rotating stage that rotates the entirety of the χ-axis rotating stage about an ω-axis, and
      a 2θ-axis rotating stage that rotates the X-ray detecting unit about the 2θ-axis,
      wherein the second φ-axis rotation drive unit rotates at a speed higher than that of the first φ-axis rotation drive unit.

2. The X-ray analysis apparatus according to claim 1, wherein the X-ray detecting unit has a slit and an X-ray detector, the X-ray detector detecting the X-ray that has passed through the slit.

3. The X-ray analysis apparatus according to claim 1, wherein the X-ray detecting unit has a slit, a first X-ray detector, and a second X-ray detector,
   wherein the second X-ray detector is a transmissive integrating ionization chamber, and
   wherein, out of the X-ray having been transmitted through the second X-ray detector, part of the X-ray that has passed through the slit is detected by the first X-ray detector.

4. The X-ray analysis apparatus according to claim 3, wherein the transmissive integrating ionization chamber is an ionization chamber.

5. The X-ray analysis apparatus according to claims 1, further comprising:
   an X-axis adjustment stage and a Y-axis adjustment stage that are disposed between the first φ-axis rotating stage and the second φ-axis rotating stage and that adjust the position of the second φ-axis rotating stage relative to the first φ-axis rotating stage in two-dimensional directions perpendicular to the φ-axis; and
   a swivel Rx axis adjustment stage and a swivel Ry axis adjustment stage that are disposed between the first φ-axis rotating stage and the second φ-axis rotating stage and that adjusts inclination of the second φ-axis rotating stage relative to the first φ-axis rotating stage.

6. The X-ray analysis apparatus according to claims 1, wherein the 2θ-axis and the ω-axis are coaxial with each other.

7. The X-ray analysis apparatus according to claims 1, wherein the ω-axis and the χ-axis are perpendicular to each other, and the χ-axis and the φ-axis are perpendicular to each other.

8. An X-ray analysis apparatus comprising:
   an X-ray source that emits an X-ray, a specimen being irradiated with the X-ray;
   a specimen holding unit that holds the specimen; and
   an X-ray detecting unit that detects the X-ray diffracted by the specimen,
   wherein the specimen holding unit includes
      a second φ-axis rotating stage that rotates the specimen about a first axis using a second φ-axis rotation drive unit,
      a first φ-axis rotating stage that rotates the entirety of the second φ-axis rotating stage about the first axis using a first φ-axis rotation drive unit, the second φ-axis rotating stage being disposed on the first φ-axis rotating stage,
      a χ-axis rotating stage that rotates the entirety of the first φ-axis rotating stage about a second axis,
      an ω-axis rotating stage that rotates the entirety of the χ-axis rotating stage about a third axis, and
      a 2θ-axis rotating stage that rotates the X-ray detecting unit about the third axis, wherein the first axis and the second axis are perpendicular to each other, and the second axis and the third axis are perpendicular to each other, and wherein the second φ-axis rotation drive unit rotates at a speed higher than that of the first φ-axis rotation drive unit.

9. A method of X-ray analysis performed in an X-ray analysis apparatus that includes a specimen holding unit that includes a second φ-axis rotating stage that rotates a specimen about a φ-axis, a first φ-axis rotating stage that rotates the entirety of the second φ-axis rotating stage about the φ-axis, the second φ-axis rotating stage being disposed on the first φ-axis rotating stage, a χ-axis rotating stage that rotates the entirety of the first φ-axis rotating stage about a χ-axis, an ω-axis rotating stage that rotates the entirety of the χ-axis rotating stage about an ω-axis, and a 2θ-axis rotating stage that rotates an X-ray detecting unit about a 2θ-axis, the method comprising:

performing an ω-axis optimization by rotating the φ-axis rotating stage while rotating the second φ-axis rotating stage at high speed; and performing a φ-axis optimization by rotating the first φ-axis rotating stage after the ω-axis optimization has been performed.

10. The method according to claim 9, wherein the ω-axis optimization and the φ-axis optimization are performed by detecting an X-ray diffracted by the specimen using a transmissive integrating ionization chamber.

11. The method according to claim 9, further comprising:

performing a 2θ-axis optimization by rotating the 2θ-axis rotating stage after the φ-axis optimization has been performed.

12. The method according to claim 11, wherein the 2θ-axis optimization is performed by detecting the X-ray that has been diffracted by the specimen, transmitted through the transmissive integrating ionization chamber and, has passed through a slit.

13. The method according to claims 9, further comprising:

performing a χ-axis optimization by rotating the χ-axis rotating stage while rotating the second φ-axis rotating stage at high speed before the ω-axis optimization is performed.

14. The method according to claim 13, wherein the χ-axis optimization is performed by detecting the X-ray diffracted by the specimen using the transmissive integrating ionization chamber.

15. The method according to claim 9, the method performing the ω-axis optimization as a second ω-axis optimization, the method further comprising:

performing a χ-axis optimization by rotating the χ-axis rotating stage, the χ-axis optimization being performed before the second ω-axis optimization and the φ-axis optimization are performed;

performing a first ω-axis optimization by rotating the ω-axis rotating stage after the χ-axis optimization has been performed;

performing a first 2θ-axis optimization by rotating the 2θ-axis rotating stage after the first ω-axis optimization has been performed; and performing a second 2θ-axis optimization by rotating the 2θ-axis rotating stage after the second ω-axis optimization and the φ-axis optimization have been performed, wherein the second ω-axis optimization and the φ-axis optimization are performed after the first 2θ-axis optimization has been performed, wherein a symmetric diffraction peak with the specimen is optimized by the χ-axis optimization, the first ω-axis optimization, and the first 2θ-axis optimization, and wherein an asymmetric diffraction peak with the specimen is optimized by the second ω-axis optimization, the φ-axis optimization, and the second 2θ-axis optimization.

16. The method according to claim 15, wherein the χ-axis optimization, the first ω-axis optimization, the second ω-axis optimization, and the φ-axis optimization are performed by detecting an X-ray diffracted by the specimen using a transmissive integrating ionization chamber.

17. The method according to claim 15, wherein the first 2θ-axis optimization and the second 2θ-axis optimization are performed by detecting the X-ray that has been diffracted by the specimen, transmitted through the transmissive integrating ionization chamber, and has passed through a slit.

18. The method according to claims 15, wherein distortion of the specimen is calculated in accordance with values optimized in the first ω-axis optimization, the first 2θ-axis optimization, the second ω-axis optimization, and the second 2θ-axis optimization.

19. The method according to of claims 9, wherein the 2θ-axis and the (0-axis are coaxial with each other.

20. The method according to claims 9, wherein the ω-axis and the χ-axis are perpendicular to each other, and the χ-axis and the φ-axis are perpendicular to each other.

* * * * *